US008728071B2

(12) United States Patent
Lischinsky et al.

(10) Patent No.: US 8,728,071 B2
(45) Date of Patent: *May 20, 2014

(54) SYSTEMS AND METHODS EMPLOYING RADIOFREQUENCY ENERGY FOR SKIN TREATMENT

(71) Applicant: EndyMed Medical, Ltd., Caesarea (IL)

(72) Inventors: Daniel Lischinsky, Ramat-Yshay (IL); Yoram Harth, Herzliyya (IL)

(73) Assignee: EndyMed Medical Ltd., Caesarea, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/779,237

(22) Filed: Feb. 27, 2013

(65) Prior Publication Data
US 2013/0165928 A1 Jun. 27, 2013

Related U.S. Application Data

(63) Continuation of application No. 13/523,300, filed on Jun. 14, 2012, now Pat. No. 8,512,331, which is a continuation of application No. 11/654,914, filed on Jan. 17, 2007, now Pat. No. 8,206,381.

(60) Provisional application No. 60/774,167, filed on Feb. 17, 2006, provisional application No. 60/759,289, filed on Jan. 17, 2006.

(51) Int. Cl.
A61B 18/14 (2006.01)
(52) U.S. Cl.
USPC .............................. 606/34; 606/41
(58) Field of Classification Search
USPC ............ 606/32–34, 41, 42; 607/101–102
See application file for complete search history.

(56) References Cited

U.S. PATENT DOCUMENTS

| 4,818,954 A | 4/1989 | Flachenecker et al. |
| 4,974,587 A | 12/1990 | Turner et al. |
| 5,334,183 A | 8/1994 | Wuchinich |
| 5,370,645 A | 12/1994 | Klicek et al. |
| 5,383,917 A * | 1/1995 | Desai et al. .................. 607/102 |
| 5,437,664 A | 8/1995 | Cohen et al. |

(Continued)

FOREIGN PATENT DOCUMENTS

| EP | 1112720 A1 | 7/2001 |
| WO | WO 95/25472 | 9/1995 |
| WO | WO 98/47436 | 10/1998 |
| WO | WO 99/56647 | 11/1999 |

OTHER PUBLICATIONS

European Search Report for Application No. EP 12 16 7932, date of completion of search, Oct. 26, 2012.

(Continued)

Primary Examiner — Michael Peffley
(74) Attorney, Agent, or Firm — Pearl Cohen Zedek Latzer Baratz LLP

(57) ABSTRACT

This disclosure relates generally to electrosurgical methods and devices. In one embodiment, an electrosurgical device is provided suitable for applying phase controlled RF energy to a treatment site. The electrosurgical device comprises a multi-electrode electrosurgical probe electrically coupled to a plurality of RF generators. Also provided are methods of use of such an electrosurgical device, as well as other electrosurgical devices. The methods and devices disclosed herein find utility, for example, in the field of medicine.

32 Claims, 15 Drawing Sheets

(56) References Cited

U.S. PATENT DOCUMENTS

| | | | |
|---|---|---|---|
| 5,542,916 A | 8/1996 | Hirsch et al. | |
| 5,556,396 A | 9/1996 | Cohen et al. | |
| 5,620,481 A | 4/1997 | Desai et al. | |
| 5,643,257 A | 7/1997 | Cohen et al. | |
| 5,693,078 A | 12/1997 | Desai et al. | |
| 5,702,386 A | 12/1997 | Stern et al. | |
| 5,755,753 A | 5/1998 | Knowlton | |
| 5,769,847 A | 6/1998 | Panescu et al. | |
| 5,817,093 A | 10/1998 | Williamson, IV et al. | |
| 5,827,294 A | 10/1998 | Mehl, Sr. | |
| 5,931,836 A | 8/1999 | Hatta et al. | |
| 5,971,980 A | 10/1999 | Sherman | |
| 5,971,982 A | 10/1999 | Betsill et al. | |
| 6,045,550 A | 4/2000 | Simpson et al. | |
| 6,050,994 A | 4/2000 | Sherman | |
| 6,059,778 A * | 5/2000 | Sherman | 606/34 |
| 6,123,702 A | 9/2000 | Swanson et al. | |
| 6,148,232 A | 11/2000 | Avrahami | |
| 6,200,314 B1 | 3/2001 | Sherman | |
| 6,228,079 B1 | 5/2001 | Koenig | |
| 6,347,251 B1 | 2/2002 | Deng | |
| 6,398,779 B1 | 6/2002 | Buysse et al. | |
| 6,413,255 B1 | 7/2002 | Stern | |
| 6,423,057 B1 | 7/2002 | He et al. | |
| 6,488,678 B2 | 12/2002 | Sherman | |
| 6,558,378 B2 | 5/2003 | Sherman et al. | |
| 6,620,157 B1 | 9/2003 | Dabney et al. | |
| 6,711,435 B2 | 3/2004 | Avrahami | |
| 6,730,078 B2 | 5/2004 | Simpson et al. | |
| 6,743,229 B2 | 6/2004 | Buysse et al. | |
| 6,889,090 B2 * | 5/2005 | Kreindel | 607/101 |
| 6,958,063 B1 | 10/2005 | Soll et al. | |
| 7,048,734 B1 | 5/2006 | Fleischman et al. | |
| 7,083,616 B2 | 8/2006 | Kawai et al. | |
| 7,166,103 B2 * | 1/2007 | Carmel et al. | 606/41 |
| 2001/0008967 A1 | 7/2001 | Sherman | |
| 2002/0156472 A1 | 10/2002 | Lee et al. | |
| 2005/0070896 A1 | 3/2005 | Daniel et al. | |
| 2005/0283148 A1 | 12/2005 | Janssen et al. | |
| 2006/0015095 A1 | 1/2006 | Desinger | |
| 2006/0047281 A1 | 3/2006 | Kreindel | |

OTHER PUBLICATIONS

International Search Report, mailing date Jun. 17, 2008 for PCT application PCT/IB2007/01585.

Written Opinion of the International Searching Authority, mailing date Jun. 17, 2008 for PCT application PCT/IB2007/01585.

\* cited by examiner

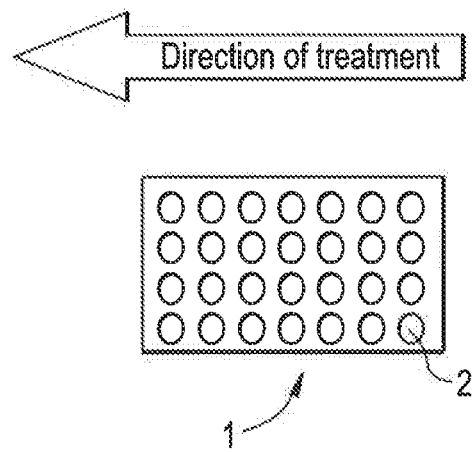
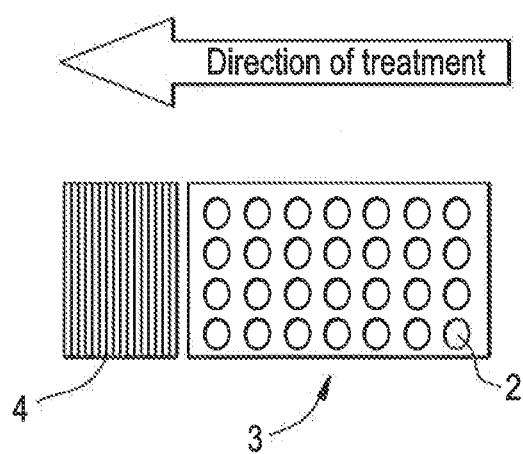

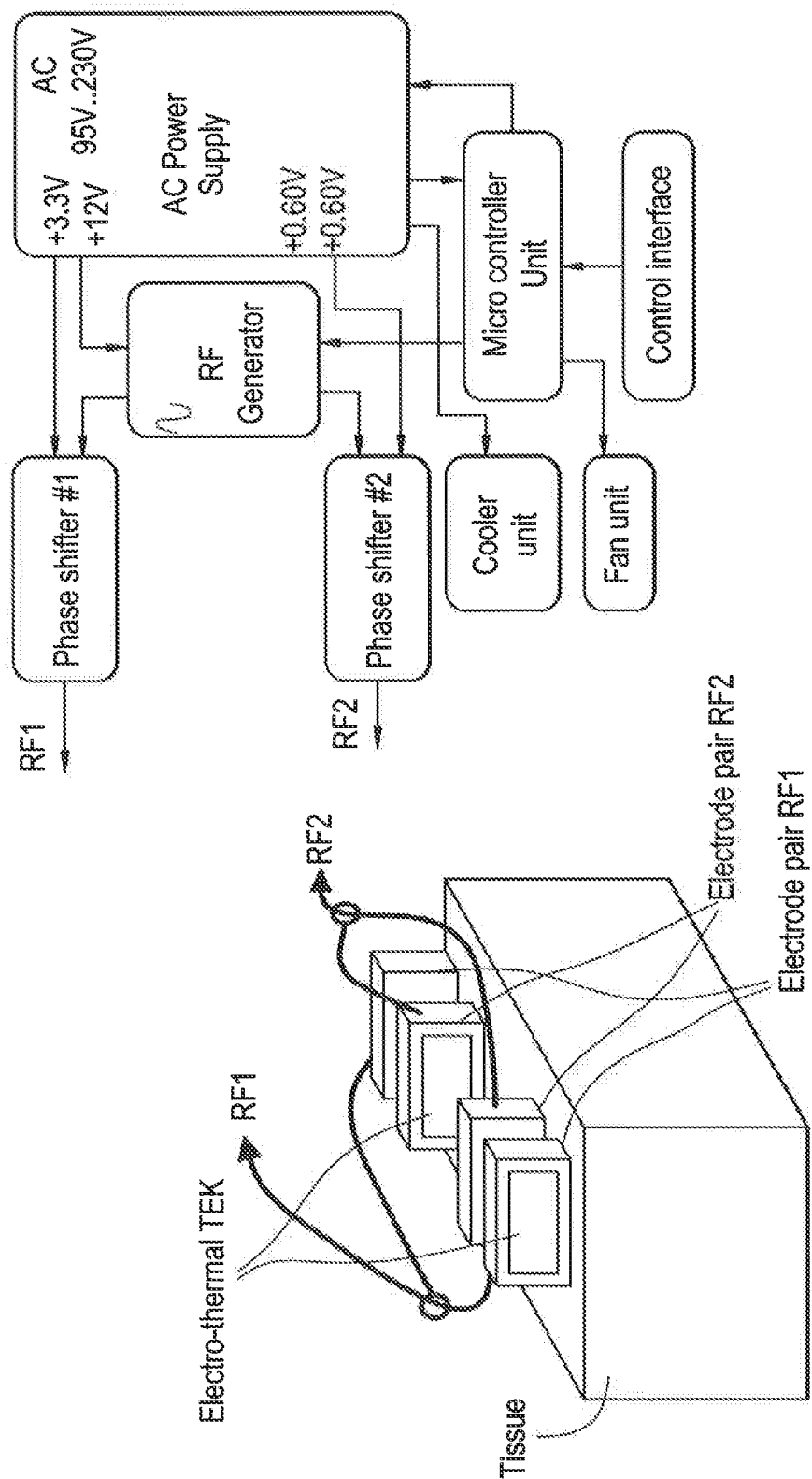

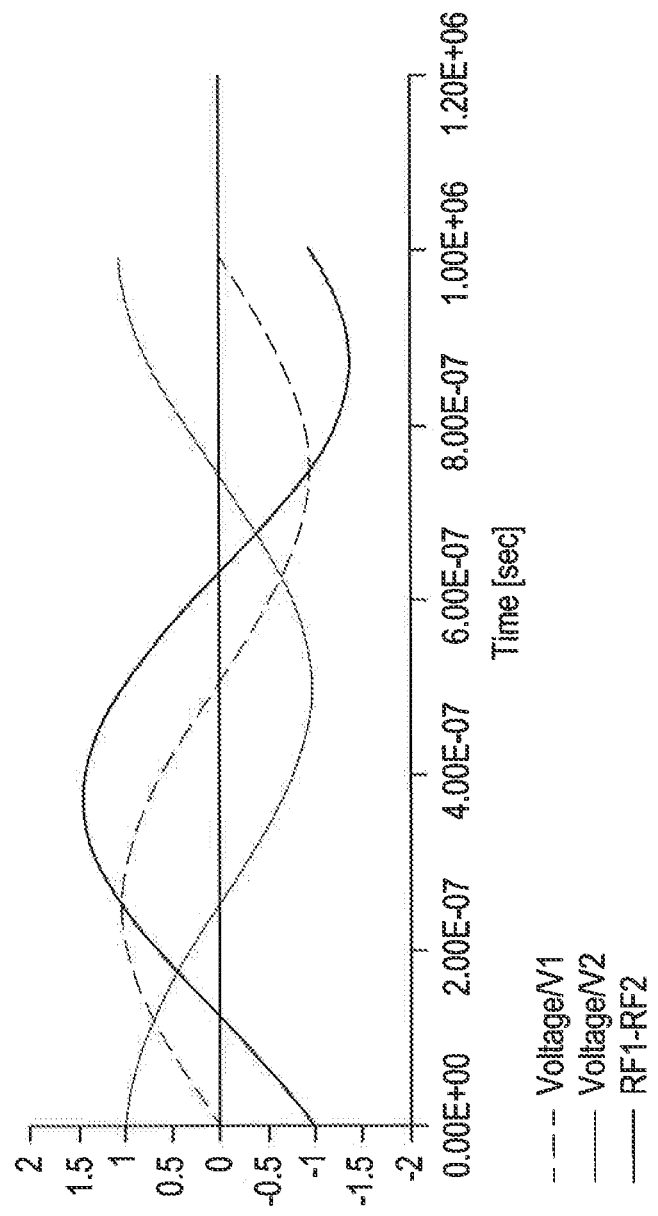

SYSTEMS AND METHODS EMPLOYING RADIOFREQUENCY ENERGY FOR SKIN TREATMENT

CROSS-REFERENCE TO RELATED APPLICATIONS

The present application is a continuation of U.S. patent application Ser. No. 13/523,300, filed Jun. 14, 2012, now U.S. Pat. No. 8,512,331, which is a continuation of U.S. patent application Ser. No. 11/654,914, filed on Jan. 17, 2007, now U.S. Pat. No. 8,206,381 issued Jun. 26, 2012, which claims the benefit of provisional U.S. patent application No. 60/774,167, filed on Feb. 17, 2006, and the benefit of provisional U.S. patent application No. 60/759,289, filed on Jan. 17, 2006, all of the disclosures of which are herein incorporated by reference in their entireties.

TECHNICAL FIELD

This disclosure relates generally to electrosurgical methods and devices. The methods and devices disclosed herein find utility, for example, in the field of medicine.

BACKGROUND

Radiofrequency (RF) devices are used to non-specifically and non-selectively ablate or heat different types of tissue. For example, in the field of dermatology RF devices are used to treat aging skin. Skin aging is associated with changes in the upper levels of the skin such as roughness of the skin due to changes in the stratum corneum and epidermis and uneven pigmentation in the epidermis. In the dermis, aging and environmental factors cause the destruction and malfunction of collagen and elastin fibers leading to the formation of wrinkles. Symptoms of skin aging in the epidermis are typically treated by ablative methods such as chemical peels or laser resurfacing. Optical radiation devices such as lasers are used to resurface large areas of the skin. While these lasers are effective in the treatment of the signs of skin aging, resurfacing the whole epidermis is often associated with side effects such as wound infections, prolonged healing times, hyperpigmentation, hypopigmentation, and scarring.

WO 05/007003 describes a method for achieving beneficial effects in a target tissue in skin comprising treating the target tissue using optical radiation to create a plurality of microscopic treatment zones in a predetermined treatment pattern. This method of resurfacing the skin, however, necessitates the use of complicated and expensive laser devices and requires special facilities, prolonged treatment times, and highly trained operators.

Radiofrequency (RF) devices are used to ablate localized skin lesions or to destroy the whole upper surface of the skin. However, whole skin resurfacing methods and devices cause burn like post treatment reactions associated with prolonged healing times, increased risk of infections, prolonged erythema, scarring, hyperpigmentation, and hypopigmentation.

U.S. Pat. No. 6,711,435 discloses a device for ablating the stratum corneum epidermis of a subject, including a plurality of electrodes, which are applied to the subject's skin at respective points. However, this device does not ablate the epidermis and thus has no effects on the signs of skin aging.

The RF devices described previously lack the efficacy and safety needed for treatment of signs of skin aging in the epidermis. Some devices resurface the whole epidermis risking multiple side effects, while others ablate only miniscule parts of the upper stratum corneum without therapeutic effects on signs of skin aging.

Symptoms of skin aging in the dermis are typically treated by non-ablative methods, including lasers, intense pulsed light, or RF devices that heat the dermis to trigger renewal of collagen fibers. In order to trigger collagen renewal, some RF devices use bipolar electrodes to increase the heat of dermal skin layers through the creation of electrical currents that flow parallel to the skin surface. These devices use active and return electrodes that are typically positioned relatively close to one another at the treatment site. In some cases, the two electrodes are located on the same electrosurgical probe, and the electrodes alternate between functioning as active and return electrodes. Other RF devices use unipolar or monopolar electrical energy for heating the deep layers of skin. These devices also use an active electrode and a return electrode. The return electrode is typically positioned a relatively large distance from the active electrode (in comparison with bipolar devices). For both unipolar and bipolar devices, current flows along the lowest impedance path between electrodes.

Other devices use a combination of optical energy and bipolar RF energy to treat the skin.

The devices described previously lack the ability to control the spatial directions, energies, and nature of the electrical energies affecting the treated area and thus lack the selectivity and specificity needed for maximum efficacy in their respective therapeutic indications. Moreover, the bipolar and monopolar RF devices lack the ability to treat the signs of aging in the epidermis. Enhanced ability to control the spatial directions and the pattern of electron flows in the treated biological tissue would allow effective therapy for additional dermatological and non-dermatological disorders such as hair removal, acne, acne scars, psoriasis, bone grafting and more.

Despite advancements in the use of optical and RF devices for treating biological tissue, there continues to be a need in the art to develop effective electrosurgical devices and methods that are suitable for treating a wide variety of conditions. An ideal electrosurgical method and related devices would be capable of selectively and specifically treating a wide variety of biological tissues and conditions effecting such tissues. Such a method and devices would be simple to use, and would have minimal adverse effects.

SUMMARY OF THE DISCLOSURE

The present disclosure is directed at addressing one or more of the abovementioned drawbacks of known electrosurgical methods and devices.

In one embodiment, then, the disclosure describes a method for delivering energy to a target site of a patient. The method comprises placing an electrosurgical probe into close proximity of the target site and delivering phase controlled RF energy to the electrosurgical probe.

In another embodiment, the disclosure describes a method for modifying living tissue. The method comprises exposing the tissue to an electric field, wherein the electric field is generated by an electrosurgical device. The electrosurgical device comprises an electrosurgical probe comprising a plurality of electrodes electrically coupled to: (i) first and second RF sources; or (ii) an RF source comprising first and second RF outputs. The electrosurgical probe further comprises means for controlling the phase between the RF energy supplied to the plurality of electrodes.

In yet another embodiment, the disclosure describes an electrosurgical system. The electrosurgical system comprises a means for applying RF energy to a target site of a patient. The electrosurgical system further comprises a generator comprising: (i) first and second RF power sources or an RF power source comprising first and second RF outputs; and (ii) a means for controlling the phase between the first and second RF power sources.

In a still further embodiment, the disclosure describes an electrosurgical system for treating living tissue. The system is configured to deliver phase controlled RF electrical energy to the living tissue.

In yet another embodiment, the disclosure describes a method for treating living tissue. The method comprises applying an electric field to a surface of the tissue by means of the electrosurgical system as described herein. The electrical energy causes tissue necrosis within a region of the tissue, the width of the region being confined to a substantially circular area of the tissue surface having a diameter in the range of about 1 µm to about 4000 µm.

In a still further embodiment, the disclosure describes a method for causing tissue necrosis. The method comprises contacting a surface of the tissue with two or more electrodes and applying an electrical potential between the electrodes. Necrosis occurs in the area between the two electrodes and is confined to a region that has a diameter in the range of about 1 µm to about 4000 µm.

BRIEF DESCRIPTION OF THE DRAWINGS

FIGS. 2a, 2b, 2c, and 2d are example illustration of electrosurgical probes as described herein.

FIGS. 9a, 9b, and 9c depict examples of electrosurgical devices as described herein.

FIG. 10 is a graph showing two RF signals having different phases as well as the signal that results from their summation.

DETAILED DESCRIPTION OF THE INVENTION

Before describing the present invention in detail, it is to be understood that unless otherwise indicated, this invention is not limited to particular electrosurgical methods, electrosurgical devices, or power sources, as such may vary. It is also to be understood that the terminology used herein is for the purpose of describing particular embodiments only, and is not intended to be limiting.

it must be noted that, as used in this specification and the appended claims, the singular forms "a," "an" and "the" include plural referents unless the context clearly dictates otherwise. Thus, for example, "a power source" refers not only to a single power source but also to a combination of two or more power sources, "an electrode" refers to a combination of electrodes as well as to a single electrode, and the like.

Unless defined otherwise, all technical and scientific terms used herein have the meaning commonly understood by one of ordinary skill in the art to which the invention pertains. Although any methods and materials similar or equivalent to those described herein may be useful in the practice or testing of the present invention, preferred methods and materials are described below. Specific terminology of particular importance to the description in the present disclosure is defined below.

As used herein, the terms "may," "optional," "optionally," or "may optionally" mean that the subsequently described circumstance may or may not occur, so that the description includes instances where the circumstance occurs and instances where it does not.

As used herein, the term "device" is meant to refer to any and all components of a system. For example, an "electrosurgical device" refers to an electrosurgical system that may comprise components such as electrosurgical probes, power sources, connecting cables, and other components.

The terms "treating" and "treatment" as used herein refer to reduction in severity and/or frequency of symptoms, elimination of symptoms and/or underlying cause, prevention of the occurrence of symptoms and/or their underlying cause (e.g., prophylactic therapy), and improvement or remediation of damage.

By "patient," or "subject" is meant any animal for which treatment is desirable. Patients may be mammals, and typically, as used herein, a patient is a human individual.

The terms "light" and "light energy" as used herein are meant to include visible, infrared, and ultraviolet electromagnetic energy.

The term "phase" as used herein refers to the phase angle of an alternating-current (AC) radiofrequency (RF) voltage (sometimes referred to as an "RF signal" or "RF voltage"). In some cases, the term "phase" also refers to the phase angle difference between two RF voltages. Accordingly, the term "phased RF energy" refers to RF energy that comprises at least two component RF voltages, wherein each component RF voltage independently has a phase.

Figure 1A:
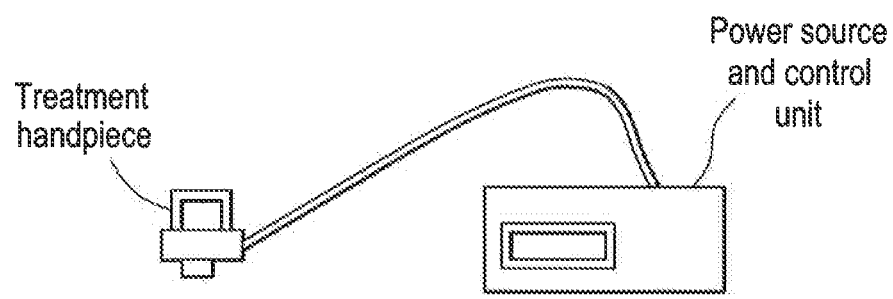
FIGS. 1a and 1b are example illustrations of the electrosurgical devices as disclosed herein.
Figure 1B:
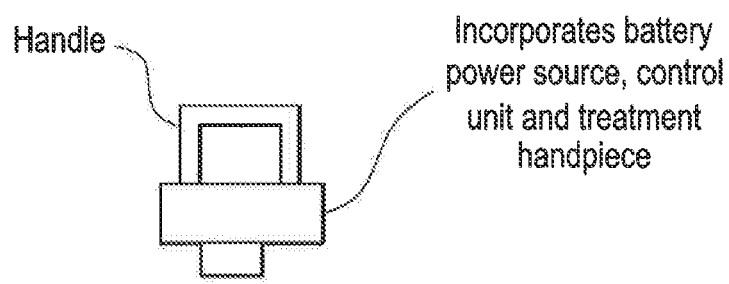

Disclosed herein are electrosurgical devices for applying phased RF energy to a treatment site such as biological tissue. Typically, the electrosurgical devices comprise an electrosurgical probe electrically coupled to a power source, as shown in FIG. 1a. The electrosurgical device can be adapted, however, for "cordless" operation, and FIG. 1b shows an electrosurgical device that combines an electrosurgical probe with a battery pack. The electrosurgical devices are adapted to promote electron conduction (i.e., electrical current) through biological tissue.

Without wishing to be bound by theory, it is believed that the phase controlled RF devices disclosed herein generate different and adjustable electrical fields within the target site. The electrical fields are capable of manipulating electrons within the target site, thereby generating selective regions of elevated temperature.

The electrosurgical probes disclosed herein employ a plurality of electrodes disposed on a treatment surface and adapted to be applied to a target biological tissue. The electrodes may be of any appropriate size or shape, and it will be appreciated that such will vary depending, for example, on the intended use. The treatment surface can be adapted to treat a variety of biological tissue surfaces. Accordingly, the treatment surface may be flat or curved. The electrodes may be uniformly disposed across the entire treatment surface, or may be concentrated in a particular section of the treatment surface. Typically, a regular pattern will be formed by the distribution of the electrodes on the treatment surface. The spacing between the electrode will depend, for example, on the probe geometry and the size of the electrodes. In general, the spacing between the centers of any two adjacent electrodes will be between about 110% and about 1000% of the diameter of the electrodes, or, for non-circular electrodes the spacing will be between about 110% and about 1000% of the maximum width of the electrodes. For treatment of human skin, for example, the center-to-center distance between adjacent electrodes may be between about 0.001 mm and about 100 mm, or between about 0.01 mm and about 25 mm. In one embodiment, adjacent electrodes are spaced apart an average of about 0.01 mm to about 0.1 mm.

One example of an arrangement of electrodes on a treatment surface is shown in FIG. 2a. Electrodes with circular cross-section are disposed in a regular pattern over a flat treatment surface. The electrodes may be either flush with the treatment surface, or the electrodes may protrude from the treatment surface.

The electrosurgical probes comprise at least 3 electrodes, and may comprise any number of electrodes greater than 3, such as 4, 5, 6, 7, 8, 9, 10, 15, 20, 50, 100, or more. For example, the probe in FIG. 2a comprises 28 electrodes.

The electrodes are electrically coupled to a power generator capable of providing a plurality of power outputs. The power generator may comprise a plurality of RF sources. The power generator may also comprise a single RF source, in which case the power generator further comprises appropriate circuitry to split the output of the RF source into a plurality of RF signals. The power generator further comprises a means for controlling the phase between any two of the power outputs. Such means for controlling will typically consist of phase shifting circuitry and the like, as will be appreciated by one of ordinary skill in the art.

The phase angle between at least two RF sources in the electrosurgical devices disclosed herein is adjustable, but it will be appreciated that the configuration of the electrosurgical devices may vary. In one embodiment, the power generator comprises two RF sources and phase shifting circuitry for adjusting the phase angle between the RF outputs of the two RF sources. In another embodiment, the power generator comprises first, second, and third RF sources. In one example of this embodiment, the phases of each RF source are adjustable, such that the phase angles between the first and second, second and third, and first and third RF sources may be independently varied. In another example of this embodiment, the first RF source has fixed output, and the phases of the second and third RF sources are adjustable. This configuration also allows adjustment of the phase angle between any two of the RF sources. In yet another example of this embodiment, the first and second RF sources have fixed output, and the phase of the third RF source is adjustable. This configuration allows adjustment of the phase angle between the first and third, and second and third RF sources. As described herein, adjustment of the phase angle between RF sources may be accomplished automatically via a feedback loop that responds to a measured electrical parameter (e.g., impendence at the target site, etc.), or may be accomplished manually via adjustment controls.

The electrosurgical probe may be disposable, such that it is sterilized upon manufacture and is intended for a one-time use. Alternatively, the electrosurgical probe may be sterilizable (e.g., autoclavable) such that it is suitable for multiple uses and, in particular, use with multiple patients.

In one embodiment, an electrosurgical device is provided that comprises a means for applying light energy to the treatment site. Such means for applying light energy include coherent sources and incoherent sources, and may include sources such as lasers, ultraviolet lamps, infrared lamps, incandescent and fluorescent lamps, light emitting diodes, and the like. The means for applying light may be attached to the electrosurgical probe or may be separate from the electrosurgical probe.

In another embodiment, the electrosurgical device may include a means for lowering the temperature of the target site. Such means include electrical cooling devices such as a heat sink and delivery ports for delivering cooling liquids or gases to the target site and surrounding tissue. For example, electrical contact cooling allows cooling of portions of the target site such as the epidermis, thereby minimizing pain and heat damage to surrounding (i.e., perilesional) skin.

Figure 2C:
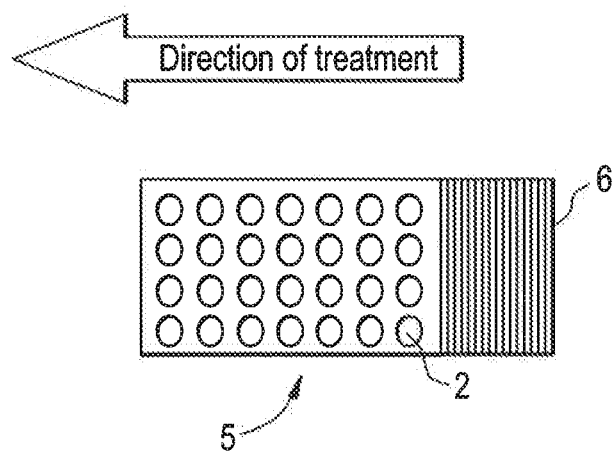
Figure 2D:
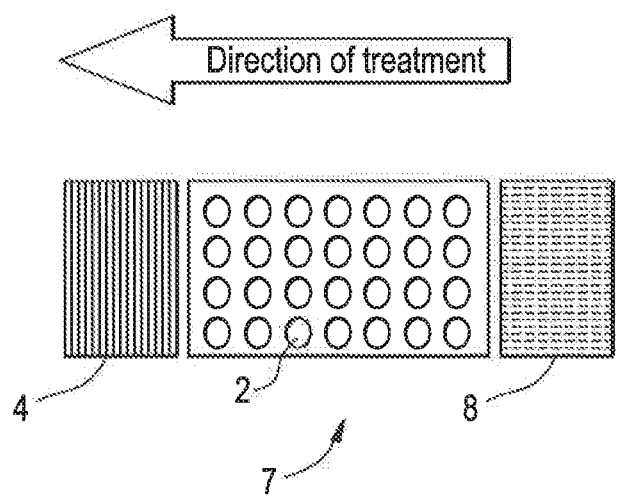

Various embodiments of the electrosurgical probes disclosed herein are shown in FIGS. 2a-2d. FIG. 2a shows the treatment surface of electrosurgical probe 1 containing no cooling devices. Twenty-eight electrodes 2 are disposed on the treatment surface. FIG. 2b shows the treatment surface of electrosurgical probe 3 containing pre-cooling device 4. FIG. 2c shows the treatment surface of electrosurgical probe 5 containing post-cooling device 6. FIG. 2d shows the treatment surface of electrosurgical probe 7 containing pre-cooling device 4 and light emitting optical source 8.

In another embodiment, the treatment portion (e.g., head or tip) of the electrosurgical probe of the device comprises a mechanism that allows all or a portion of the electrosurgical probe to mechanically vibrate during use. Such vibrations allow the treatment site to be massaged or otherwise soothed. This feature is especially preferred when the device is used to treat cellulite as described herein.

The electrosurgical device may comprise a means for measuring an electrical characteristic, and optionally a feedback loop that allows the electrosurgical device to adjust the supplied electrical energy in response to the measured electrical characteristic. Such electrical characteristics include the electrical impedance and/or admittance of the target site, the current flowing between electrodes, the electrical potential between electrodes, output voltages and phases of the RF sources, and phase differentials between RF sources. Such measurements may be taken in real time as the electrosurgical probe is in close proximity to the target site, allowing the feedback loop to regulate the power supplied by the electrosurgical device to achieve the desired result.

In one embodiment, the electrosurgical device is adapted for treating the skin. The device generates an electric field which causes a current to flow through the stratum corneum, epidermis, and/or dermis, and comprises a means for reducing or increasing the power dissipated in the stratum corneum in response to a variation in a measured electrical characteristic. Such electrical characteristics may be selected from: a magnitude of the current; a time-integration of the current; a first time-derivative of the current; and a second time-derivative of the current. It will be appreciated that these electrical characteristics may be measured in biological tissues other than the stratum corneum when skin is not the target site.

Characteristics of the electrodes may be independently measured and monitored by appropriate circuitry. Furthermore, the RF power sources may be adapted to modify the electric field generated by the electrodes so as to reduce the current through one or more of the electrodes, substantially independently of the current through any of the other electrodes.

The electrosurgical devices described herein are useful in methods for delivering energy to a target site of a patient. Target sites suitable for the application of electrical energy using the devices disclosed herein include biological tissues such as skin, mucous membranes, organs, blood vessels, and the like. Energy is delivered to the target site via an electrosurgical probe, which is placed in close proximity to the target site. By "close proximity" is meant that the probe is placed close enough to the target site to have a desired effect (e.g., tissue ablation, warming of the target site, etc.). In one embodiment, the electrosurgical probe is placed in contact with the target site.

With the electrosurgical probe in close proximity to the target site, an RF electrical potential is applied across two or more (typically three or four or more) electrodes present on the electrosurgical probe. This potential may, in some cases, cause a current to flow within the target site and between the electrodes. In addition or in the alternate, the potential causes an electric field to be applied to the target site. By employing a plurality of RF sources and at least three electrodes, characteristics of the electric field (e.g., intensity, direction, and the like) can be manipulated by controlling the phase angle ($\phi$) between the RF sources. The electrical field (F) generated by the electrosurgical probe is proportional to the phase between the RF sources and other electrical parameters of each RF source. The polarity of this electrical field will vary according with the RF sources. These variations will attract and consequently move free electrons, thereby heating at least a portion of the target site. In another embodiment of the device these free electrons will tend to flow on the more heated paths in the treated area. Which it is established using the light, flash or laser beam, as described herein.

In one embodiment, the target site is skin, and the electrosurgical device is placed in close proximity to the surface of the skin so as to generate an electric field that causes a current to flow through the stratum corneum, epidermis, and dermis. The induced electrical current may flow between electrodes, but may also have a significant component (e.g., 10%, 25%, 35%, 50%, 75% or more) in the direction that is perpendicular to the skin's surface. By creating an electrical current within the skin, the devices disclosed herein are able to increase the temperature of the skin, and in some cases, ablate one or more layers of skin. For example, the devices are useful in fully or partially ablating the surface of the skin. The devices are also useful in partially or fully ablating one or more layers below the surface of the skin.

In one embodiment, the electrosurgical devices may be used to non-homogeneously increase the temperature of biological tissue as described herein. In another embodiment, the electrosurgical devices may be used to increase the temperature of biological tissue within a narrow region relative to the size of the electrosurgical probe that is employed.

Figure 3:
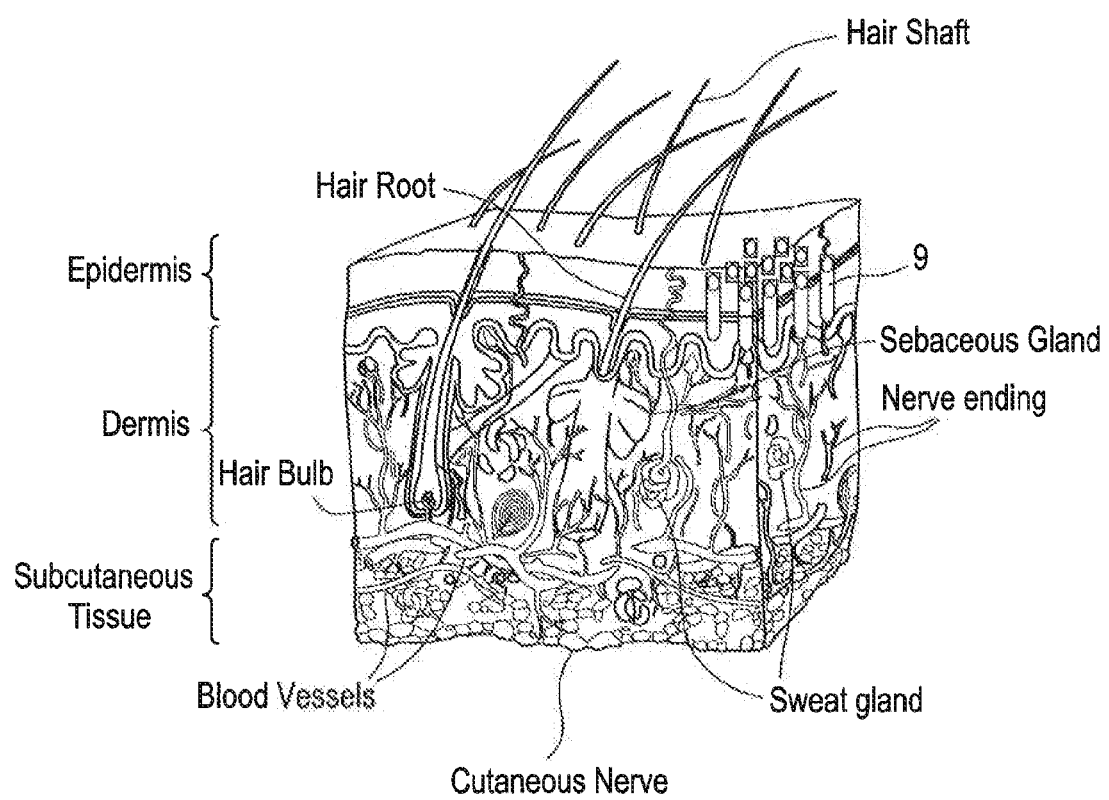
FIG. 3 is an example illustration of focal damage regions as formed by the methods and devices disclosed herein.

In one embodiment, the electrosurgical devices of the disclosure may be adapted to create one or more focal damage regions at the target site. Focal damage regions are isolated regions within the target site wherein tissue necrosis occurs. The sizes, locations, number, relative arrangement, and other factors of the focal damage regions are determined by the physical and electrical parameters of the electrosurgical devices, as well as operating conditions of the devices when in operation. Although focal damage regions may be created at any of the target sites described herein, the remaining discussion pertaining to this embodiment will primarily use human skin as an illustrative but non-limiting example. FIG. 3 shows an illustrative example of a plurality of focal damage regions 9 created in skin tissue.

Without wishing to be bound by theory, it is believed that the electrosurgical devices disclosed herein are able to create focal damage regions as a result of the adjustability of the phase angle between the RF sources. The RF sources are electrically coupled to electrodes on an electrosurgical probe; adjustment of the phase angle between RF sources causes variations in the electric field that is created in the vicinity of the electrodes. Such variations include areas of intensities and areas of weaknesses in the strength of the electric field, and may be used to manipulate electrons within the target site. Thus, appropriate modulation and adjustment of the phase between RF sources is used in the present disclosure to create heterogeneous electrical currents within the target site. Such electrical currents create regions of elevated temperature and are capable of creating tissue necrosis in the focal damage regions. Therefore, the temperature of the target site is proportional to the phase of the RF sources that are connected to the electrodes.

The dimensions of the focal damage regions may be varied as desired and as appropriate for the intended application. For example, in treating human skin, the focal damage regions may be substantially columnar and perpendicular to the surface of the skin being treated. The columns may begin at or below the surface of the skin and extend to some depth below the surface. Therefore, the columns have proximal ends and distal ends, wherein the proximal end is either at the surface of the skin or nearest the surface of the skin, and the distal end is furthest from the surface of the skin. When not at the surface of the skin, the proximal ends of the columns may be located about 0.1, 1, 2, 3, 4, 5, 10, 25, or 50 µm below the surface of the skin. The distal ends of the columns may be located about 1, 5, 10, 25, 50, 100, 1000, 2000, or 4000 µm below the surface of the skin. The width (i.e., diameter) of the columns may also vary, and may be between about 1 µm and about 7000 µm, or between about 10 µm and about 4000 µm. For example, the columns may be at least 1, 10, 20, 30, 40, 50, 100, 150, 200, 250, 500, 800, 1000, 2000, or 5000 µm in width. In one embodiment, the focal damage regions have widths that are in the range of about 50-100 µm, or about 50-70 µm. Tissue damage within the focal damage regions may be isolated within the upper layers of skin such as within the stratum corneum, or may be limited to skin cells located below the stratum corneum. Tissue damage may also extend across a plurality of layers of skin. Focal damage regions created by the electrosurgical devices disclosed herein may therefore extend through the stratum corneum and into the underlying layers of the epidermis and dermis. Focal damage regions may also be limited to the layers of the epidermis and dermis that are below the stratum corneum. Focal damage regions may be confined to the stratum corneum. Focal damage regions may also be confined to the stratum corneum and epidermis. Focal damage regions may also be confined to the stratum corneum, epidermis, and dermis. In general, the depth of the focal damage region may be selected by the operator of the device.

It will be appreciated that the focal damage regions may have shapes other than columnar, such other shapes including pyramidal, egg-shaped, or spherical. Furthermore, the cross-section of the focal damage regions (i.e., a cross-section taken parallel to the surface of the skin) may have any shape, including regular shapes such as circular, square, oval, triangular, polygonal, as well as irregular shapes.

Limitation of tissue necrosis to within the focal damage regions allows close control of the total area of tissue that is damaged. By adjusting the density and physical dimensions of the focal damage regions (which is accomplished by adjusting the phase relationship between electrodes, the RF power delivered to the electrodes, and other factors as described herein), the amount of damaged skin can be controlled. For example, using the methods disclosed herein, at least about 1%, 5%, 10%, 15%, 20%, 25%, 50%, or 75% of the tissue in the treated region is damaged.

Another characteristic of the focal damage regions is density—i.e., the number of focal damage regions that are created per unit area of tissue at the target site. Typical densities are at least about 10, 100, 200, 500, 1000, 2000, or 3000 $cm^{-2}$. In one embodiment, the density of focal damage regions is within the range of about 100-3000 $cm^{-2}$. Since the focal damage regions may be located entirely below the surface of the tissue at the target site, the density of focal damage regions can also refer to the number of regions in a unit area of a slice of the tissue at the target site. Most conveniently, such a slice of tissue will be parallel to the surface of the tissue at the target site. Again, without wishing to be hound by theory, the density of focal damage regions is a function of the number and density of electrodes, the phase relationship of the RF energy applied to the electrodes, operating conditions, and other factors that will appreciated by the skilled artisan.

Furthermore, the focal damage regions can be created in a pattern in the target region. As with focal damage region density, the orientation of focal damage regions at the target site is a function of the number and density of electrodes, the phase relationship of the RF energy applied to the electrodes, operating conditions, and other factors that will appreciated by the skilled artisan.

The amount of energy required to create each focal damage region will vary with operating conditions, type of biological tissue, size of the damage region, and other factors. In one example, the amount of energy delivered to create each damage region is about 1 $mJ*cm^{-3}$.

It will be appreciated that the physical dimensions, density, total number, and distribution pattern of the focal damage regions may vary depending on the intended application. The number and arrangement of electrodes, the phase of the RF energy applied to the electrodes, and other factors are selected based on the desired therapeutic effect.

Figure 4:
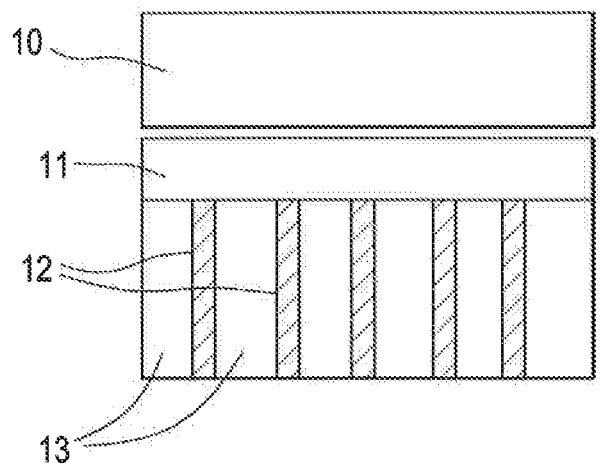
FIG. 4 is an example illustration of focal damage regions that are located entirely below the surface of the tissue at the treatment site.
Figure 5:
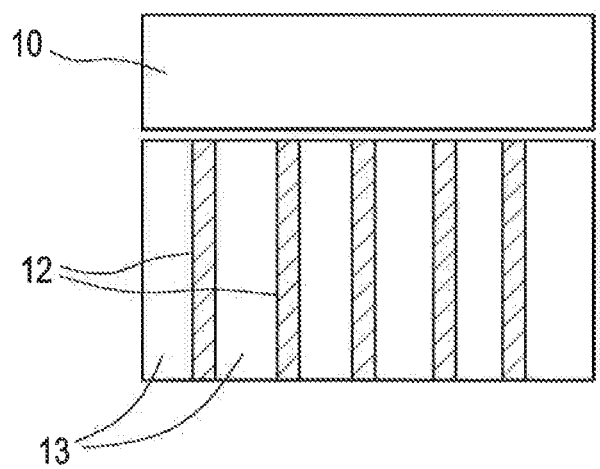
FIG. 5 is an example illustration of focal damage regions that begin at and extend below the surface of the treated tissue.

FIG. 4 shows a graphical representation of focal damage regions having proximal ends located below the surface of the tissue being treated by treatment probe 10. The region of tissue 11 between the proximal ends of focal damage regions 12 and the surface of the tissue is maintained at a cooler temperature compared with the tissue in the focal damage regions. Regions of tissue 13, located between focal damage regions 12, are also cooler than the tissue within the focal damage regions. FIG. 5 shows a graphical representation of focal damage regions 12 that extend downward (i.e., deeper into the tissue) from the surface of the tissue.

The electrosurgical probe may be translated (i.e., moved) parallel to the skin surface during the application of electrical energy to the skin. Such translation may occur with the probe either in contact with the skin or in close proximity to the skin. Translation of the probe allows for enlarged areas of treatment, improved heat dissipation, and other benefits as will be appreciated by the skilled artisan. The RF sources can also be programmed and controlled, using standard control circuitry, to apply RF energy to the electrodes in a time-dependent fashion, such that specific patterns of focal damage regions are created based on the rate and direction of translation of the electrosurgical probe.

For the treatment of lesions, scars, regions of pigmentation, etc., the pattern of focal damage regions can be predetermined using, for example, an image of the lesion acquired by digital imaging techniques and transferred to a control unit integrated with the electrosurgical device. For example, in a method for treating acne on a patient, the acne can be photographed and the electrosurgical device appropriately preprogrammed to ablate only lesions with specific lesions or pimples. Other examples include creating focal damage regions only on or near psoriatic lesions, or only in the region of a skin tattoo. In another example, the device is used to treat a patient with melasma having hyper-pigmented areas on part of the face. The electrosurgical device may be programmed to ablate the whole face with low depths of ablation. Alternatively, areas of the face characterized by greater hyper-pigmention may be treated with a higher density of focal damage regions while areas of the face that are characterized by less hyperpigmentation may be treated with a lower density of ablated regions.

The tissue within the focal damage regions may be wholly or in part ablated or damaged. Regions of tissue between the focal damage regions will typically be heated due to dissipating heat from the electrodes, although such regions will not typically be ablated or permanently damaged.

In some embodiments, treatment of conditions of the skin using focal damage regions as described herein has the advantage of minimizing healing times due to minimized damage to the tissue surrounding the focal damage regions.

In addition or as an alternative to creating focal damage regions, electrical energy applied via the electrosurgical devices disclosed herein may be used to heat, but not destroy and/or damage, the target site. For example, when the target site is skin, heat may be applied to effect collagen remodeling in a method for treating wrinkles.

Phase controlled RF devices and methods as disclosed herein may be combined with other sources of energy. In some embodiments, the use of additional forms of energy allow synergistic effects for treatment of conditions such as skin disorders, skin aging and hair removal. For example, focused ultrasound energy may cause micro-vibrations in susceptible living tissue. The micro-vibrations caused by the ultrasound differ for different types of tissue (e.g., skin; keratinocytes or epidermal cells, hard keratin such as the shaft of hairs, etc.). Since focused ultrasound energy can differentiate physical properties of living tissue (e.g., treated from untreated tissue during electrosurgical procedures, adipose subdermal cells from connective tissue cells, etc.), it can amplify the selectivity of the effects of phase controlled RE energy. In one embodiment of the methods and devices disclosed herein, phase controlled RF and ultrasound energy are used to treat tissue. Examples of uses for the combination of phase controlled RF and ultrasound energy include the removal of hair and therapy of cellulite hair (e.g., hair removal or therapy that is safer and more efficient than existing methods).

The methods disclosed herein may further comprise a pretreatment step such as: treatment with a topical anesthetic; cooling; and treatment with light energy. Topical anesthetics such as lidocain and the like may be applied as needed, such as 30-60 minutes prior to treatment with the electrosurgical device. Cooling of the target site as a pretreatment step may involve application of cooling agents such as gels, liquids, or gases. Examples include water and saline solutions, liquid nitrogen, carbon dioxide, air, and the like. Cooling may also involve electrical contact cooling. Typically, cooling of the target site is accomplished just prior to treatment with the electrosurgical probe, and has the effect of reducing pain and unwanted heat damage to the tissue surrounding the target site. Pretreatment with light energy may be accomplished using a light source integrated with the electrosurgical probe or with a separate light source, as described herein. Light energy is capable of effecting photothermolysis, and is useful in selectively heating regions of the target area. Accordingly, light energy can be used in conjunction with the electrosurgical devices. For example, regions of darker coloration such as hair and skin characterized by the presence of relatively large amounts of melanin (e.g., moles, hyperpigmented lesions, and the like) may be selectively heated, as such areas will absorb more light energy compared with regions with less pigmentation. Light energy may also be used to create preferred conduction pathways for the electrical currents that are produced by the electrosurgical probes described herein. Methods of treatment using light energy as well as the electrosurgical devices disclosed herein are particularly suitable for the treatment of hyperpigmented lesions, melasma, lentigines, wrinkles, and acne scars, as well as in hair removal, and the clearing of vascular lesions.

After treatment of the target site with the electrosurgical devices described herein, certain post-treatment steps may also be taken. Such post-treatment steps include treatment with a topical anesthetic as described above, and cooling of the target site and surrounding tissue as described above.

The electrosurgical methods and devices disclosed herein may also be used in conjunction with an additional means for applying energy such as light and/or ultrasound energy to the target site. For example, the electrosurgical probe may comprise an optical light source (e.g., lasers, incandescent lamps, gas-discharge lamps, and the like), a high-frequency ultrasound source, an infrared light source, an ultraviolet light source, or any combination thereof. Such additional means for applying energy may be electrically coupled to the same power source(s) that provide power to the electrodes of the electrosurgical probe, or may be electrically coupled to a separate power source.

The methods and devices disclosed herein are useful in the field of electrosurgery in general, and more specifically in procedures that are suitable for treatment using RF energy. For example, the methods and devices disclosed herein may be employed in procedures useful in the treatment of medical and aesthetic disorders and conditions affecting a patient's skin and subcutaneous tissue, including the following: skin resurfacing procedures; lessening the appearance of or removal of pigmentations; lessening the appearance, removing, or otherwise treating cellulite; therapy or removal of wrinkles, vascular lesions, scars and tattoos; hair removal and hair transplant procedures; treatment of skin cancer; skin rejuvenation; treatment of acne and psoriasis; debridment of chronic skin ulcers; and blepharoplasty procedures.

The methods and devices disclosed herein are also useful in treating the signs of skin aging, including treatment of skin roughness, uneven pigmentation, wrinkles, and dilated capillaries.

Other applications for the devices and methods disclosed herein, and in particular the creation of focal damage regions in the target site, include removal of aging or diseased skin, thereby allowing fast regeneration by the non-ablated skin of the surrounding areas.

Many of the conditions and methods of treatment mentioned above make use of the devices of the disclosure and their ability to selectively heat tissue below the surface of the tissue being treated. For example, the devices disclosed herein are useful in methods for treating wrinkles and other signs of aging. Warming the collagen below the surface of the skin causes the collagen molecules to reorient on a molecular level, thereby eliminating or reducing the presence of wrinkles. The use of phase-controlled RF allows selective heating of regions of collagen without causing heating or damage of surrounding areas.

Figure 6:
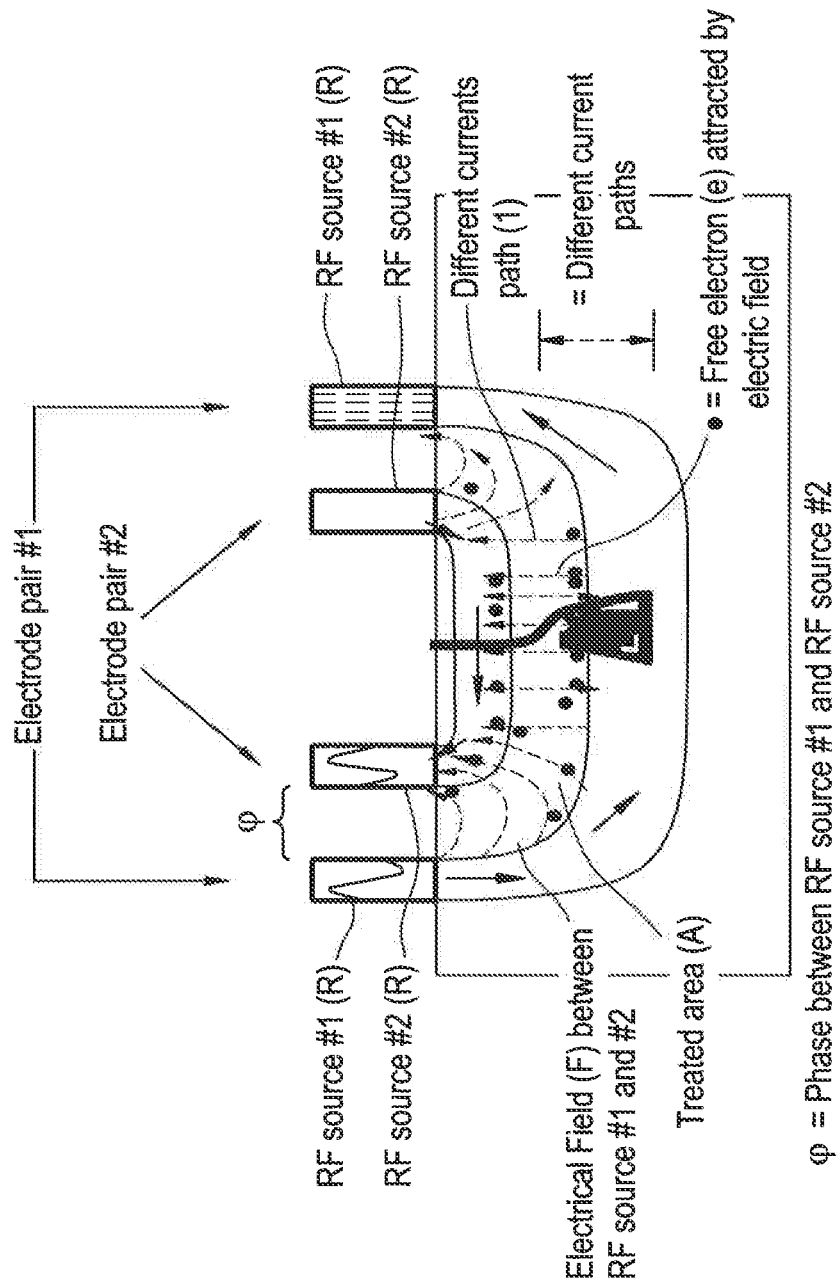
FIG. 6 is an example illustration of the application of phase controlled RF energy to skin surrounding a hair follicle.
Figure 7:
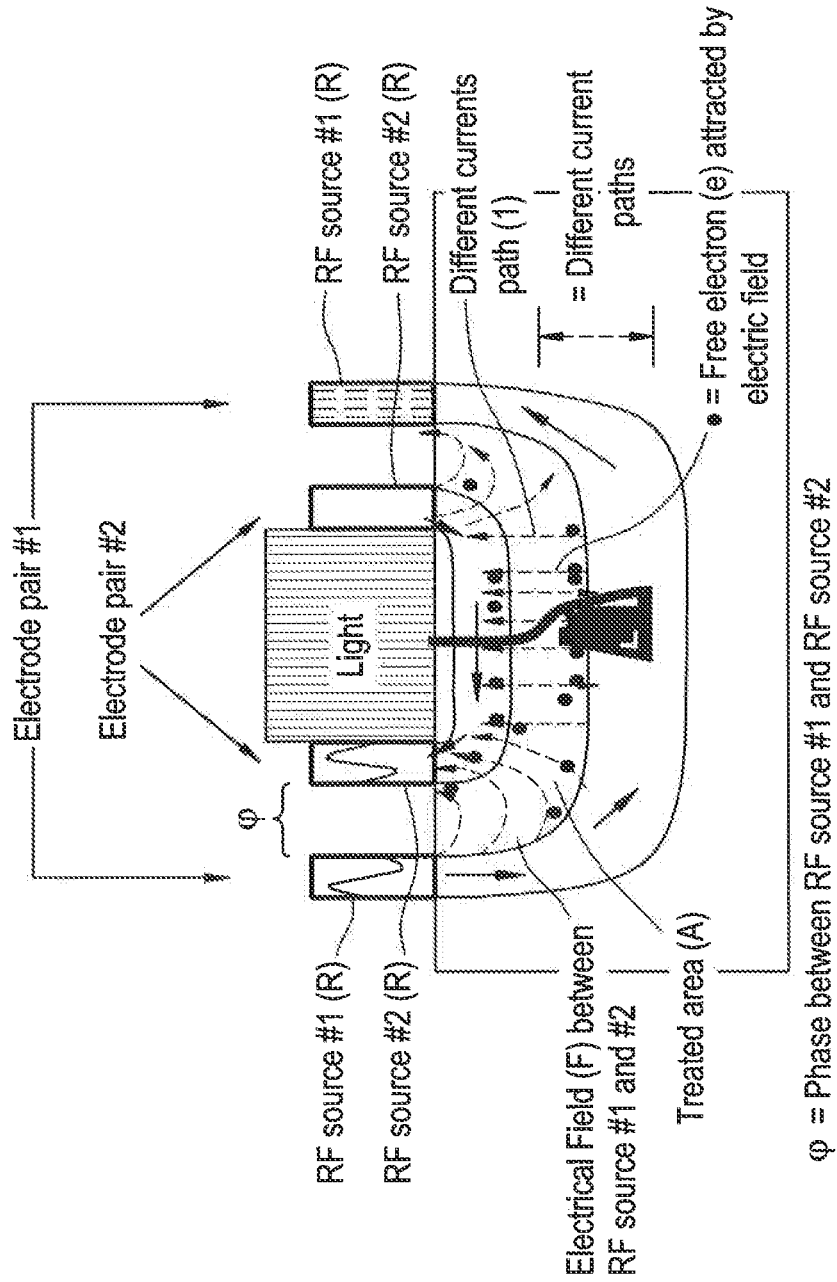
FIG. 7 is an example illustration of the application of energy in the form of phased RF and light energy to skin tissue surrounding a hair follicle.
Figure 8:
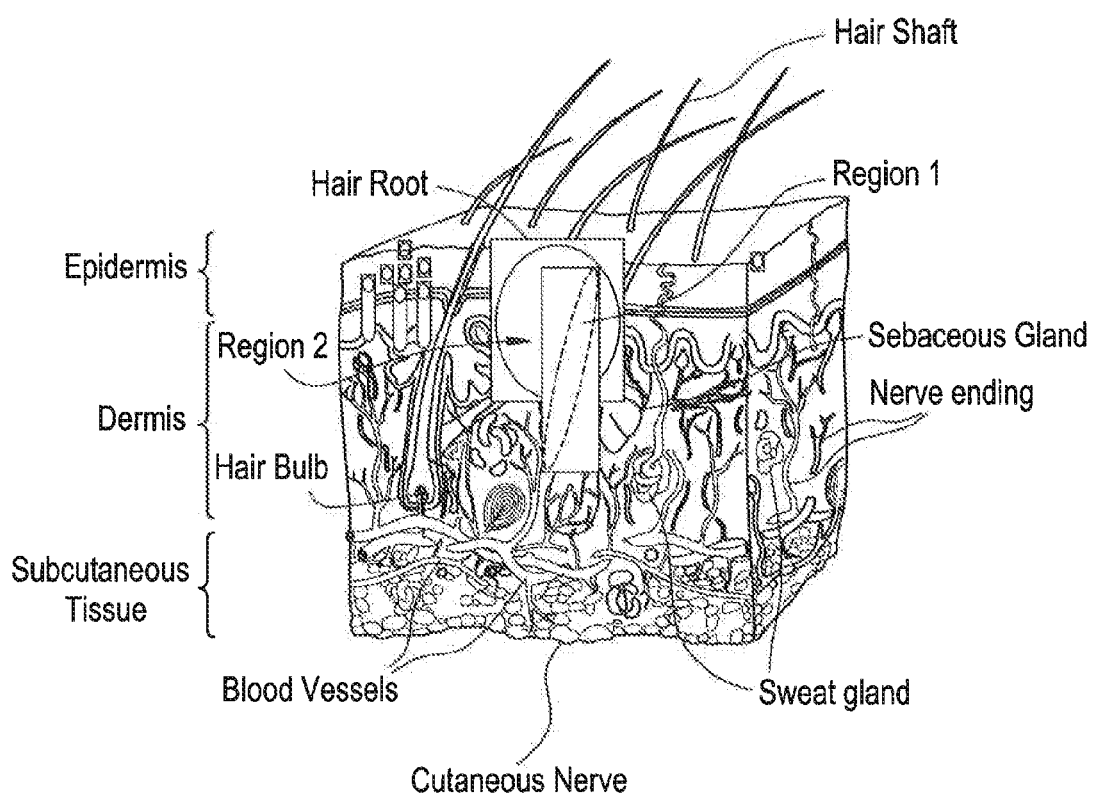
FIG. 8 is a representation of skin tissue showing the effect of combining phased RF energy with optical photoselective light energy.

In another example, the devices disclosed herein are useful in methods for removing hair and for methods of hair transplantation. The phase-controlled RF can be used to create electric fields that specifically and selectively heat hair and hair follicles, particularly when such hair and hair follicles are located between electrodes such as is shown in FIG. 6. Furthermore, treatment of hair (in addition to other methods of use) can benefit by the use of light energy in addition to the electrosurgical probe, as disclosed herein and shown in FIG. 7. FIG. 8 further shows the effects of combining light energy with phased RF energy in treating skin and hair or hair follicles therein. In FIG. 8, heat from the light source accumulates in the melanin rich hair and hair follicle (Region 1), supplementing heat from RF energy. This enhances selectivity, thereby allowing selective warming and/or damage to hairs with decreased warming and/or damage to the surrounding, relatively melanin poor areas (Region 2).

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

It is to be understood that while the invention has been described in conjunction with the preferred specific embodiments thereof, that the foregoing description as well as the examples that follow, are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains.

Example 1

Example Configurations of Electrosurgical Device

Figure 9A:
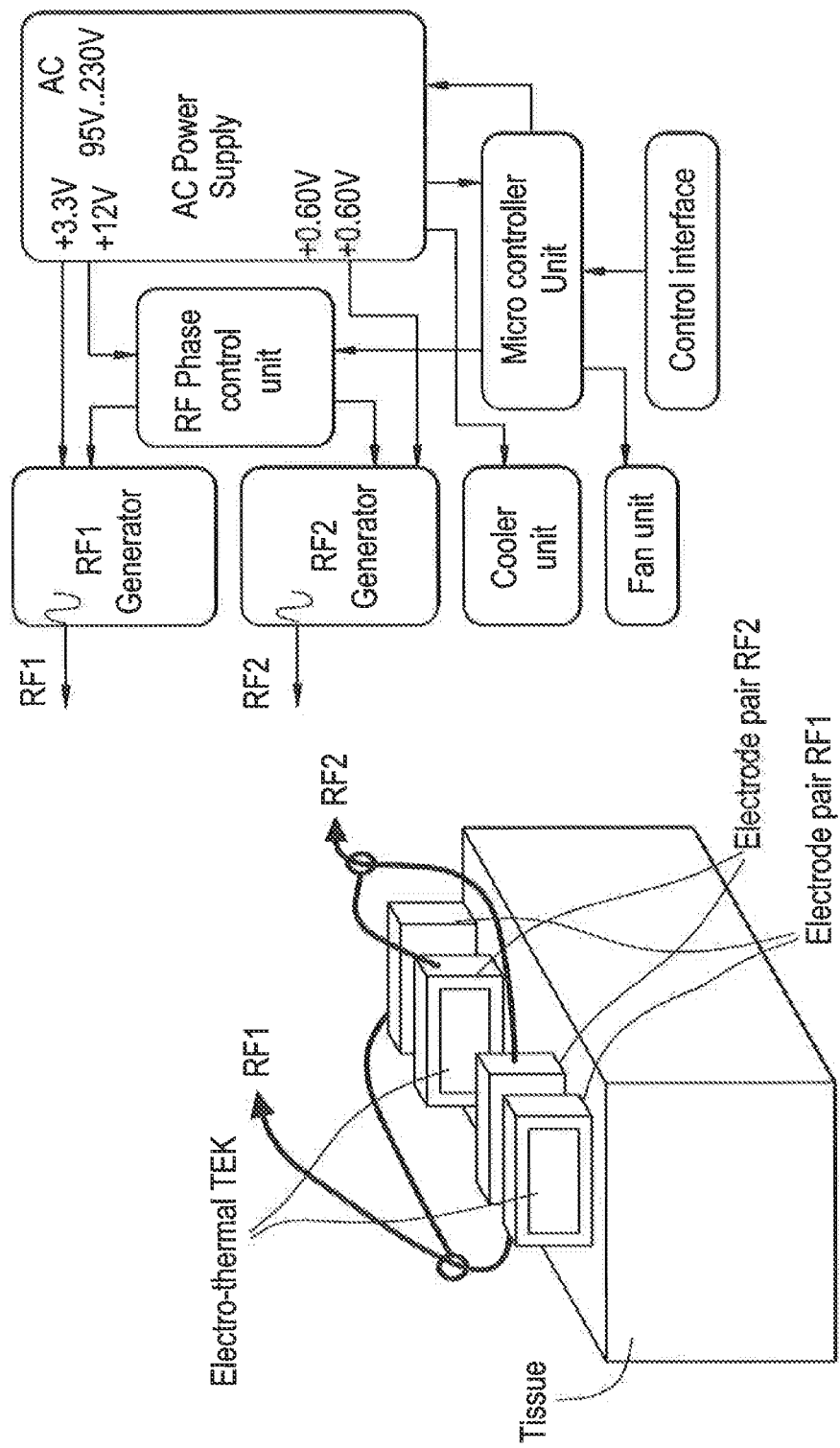
Figure 9C:
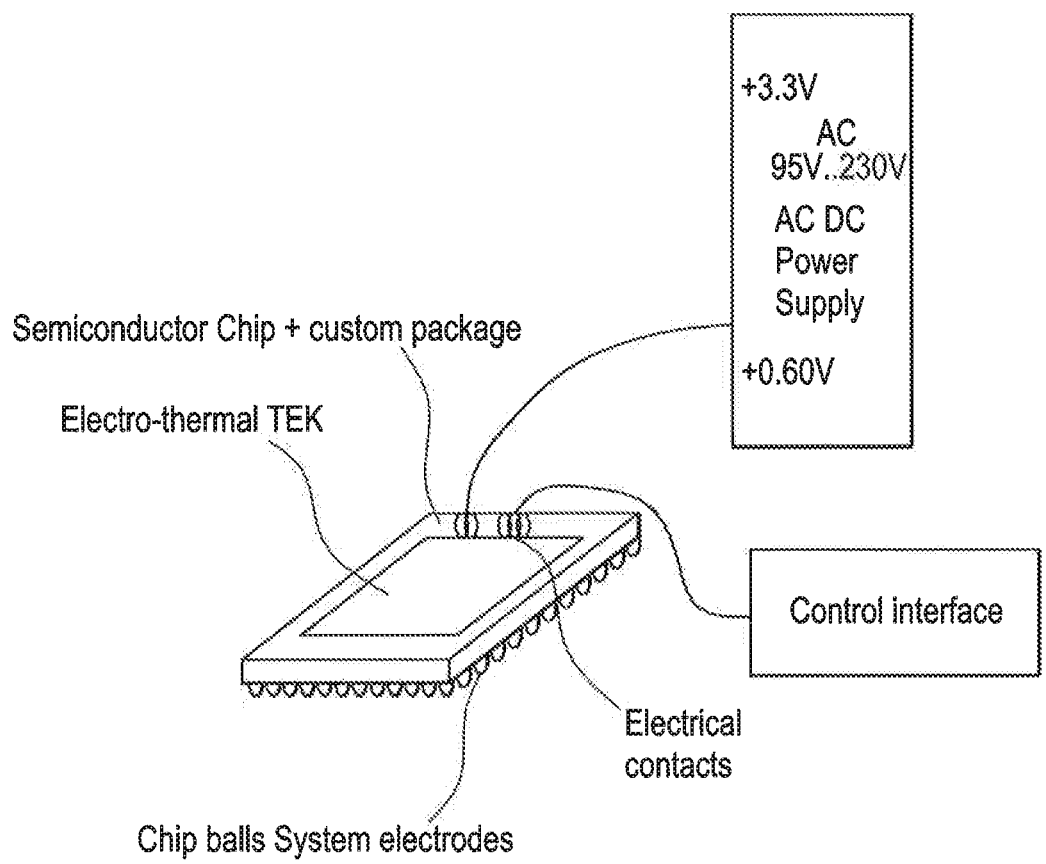

Three example configurations of phase controlled RF devices are shown in FIGS. 9a, 9b, and 9c. In FIG. 9a, a phase controlled RF (PCRF) device with only four electrodes is shown. The electrodes are connected as two pairs, labeled RF1 and RF2. Voltages V1 and V2 are applied to RF1 and RF2, respectively, using two independent RF generators. Examples of V1 and V2 are shown in FIG. 10. The voltage relation between V1 and V2 is described by equation (1).

$$V1 = V2 + \phi \tag{1}$$

Allowing equations (2)-(5) to be assumed as follows, $$V1 = V_0 \sin(2\pi ft + \theta) \tag{2}$$

$$V2 = V'_0 \sin(2\pi ft + \Psi) \tag{3}$$

$$V_0 = V'_0 \tag{4}$$

$$\phi = \theta - \Psi \tag{5}$$

then $V_{O1}$ can be expressed as in equation (6)

$$V_{O1}=2\times V\sin(2\pi ft+\theta)\sin(2\pi ft). \quad (6)$$

Figure 11:
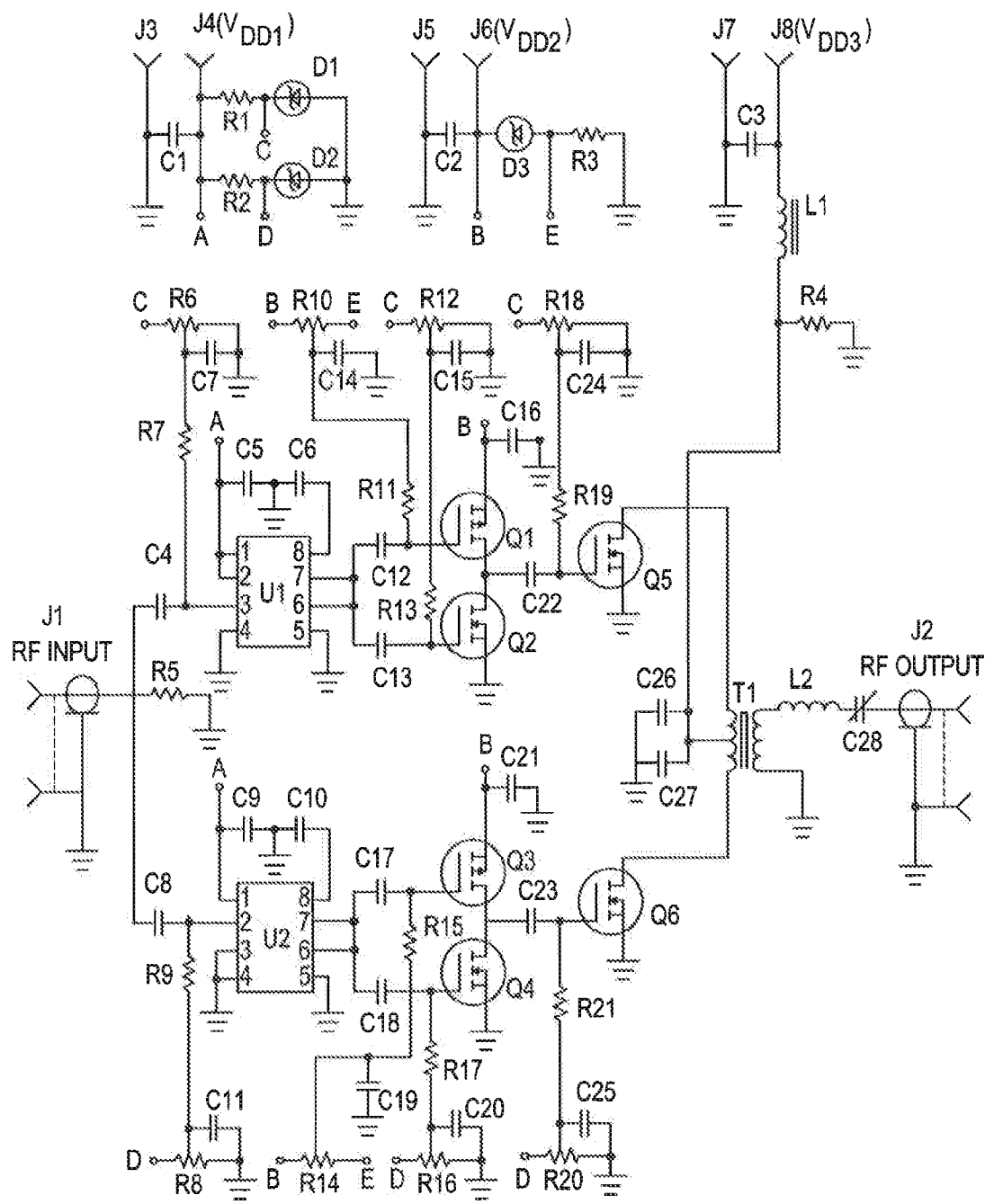
FIG. 11 shows a circuit diagram for a typical Class D type RF generator.

$V_{O1}$ is the equivalent internal potential that is used to manipulate electrons within the target site. The phase between the RF generators is controlled by the RF Phase Control Unit, also shown in FIG. 9a. Each RF generator is capable of delivering, for example, up to 500 watts to a typical load of 50 ohms at a frequency of 1 MHz, although it will be appreciated that such values may be greater or lesser as appropriate. Each RF generator has different inputs to control: (1) the power out of the unit; (2) the phase of the RF signal; (3) pulse duration; and (4) ON/OFF function. The device shown in FIG. 9a may be implemented in a variety of ways, and it will be appreciated that the efficiency of the unit (i.e., Output Power as a ratio to Input Power) will vary accordingly. A Class D type RF generator is used, in one example, to provide a device with high efficiency (~90%). FIG. 11 shows a typical Class D type RF generator.

Figure 12A:
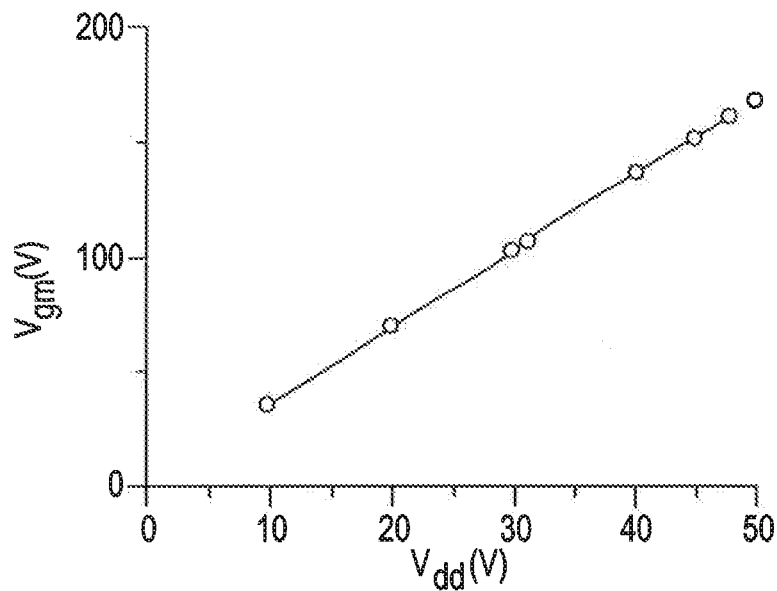
FIG. 12a is a graph illustrating the DC gain for a DC input voltage between 10 to 50 volts for the amplifier of FIG. 11.
Figure 12B:
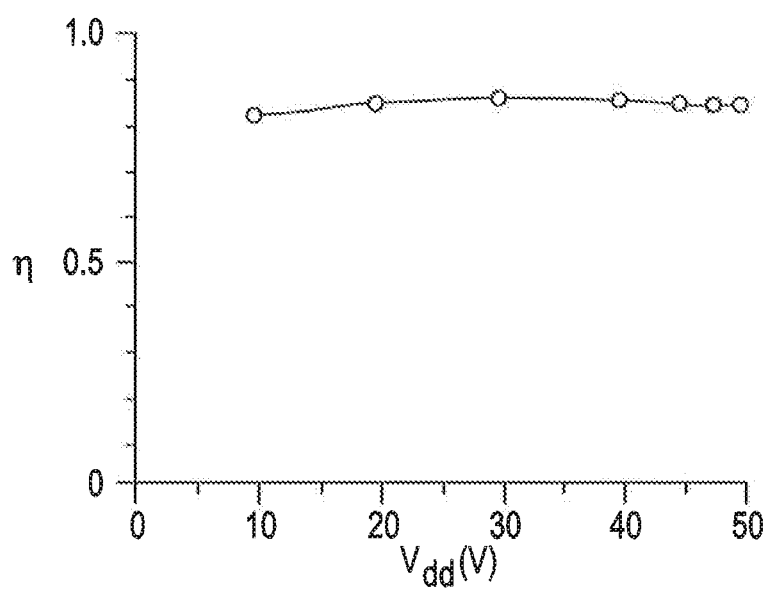
FIG. 12b illustrates the efficiency (p) of the amplifier of FIG. 11 for different input DC voltage between 10 to 50V.

The RF Phase Control Unit is a low power unit that sets the phase of each RF generator unit. This unit implements a simple square wave generator where the phase of this square wave is set by a resistor-capacitor (RC) circuit or in a digital manner by setting the appropriate register of the square wave generator chip. Examples of this kind of semiconductor chip are chips named by the number 555 or 556 (dual 555) or any common phase-locked loop (PLL) chips. Another function of the RF Phase Control Unit is to control the power out of the RF generator units (RFGUs), which is done by controlling the input voltage supplied to the RFGUs. The output power of an RFGU is proportional to the input voltage (see FIG. 12a). The input voltage is set on the AC power supply unit.

In the device shown in FIG. 9a, the voltage supplied by the AC power supply unit is controlled by the microcontroller unit. In addition, functions such as ON/OFF, pulse duration, etc, are define on the microcontroller unit and transmitted to the Phase Control Unit (PCU), which in turn controls the RFGUs.

The device in FIG. 9a also includes an Electrical Cooler Unit (ECU). In one embodiment, this unit is a controlled power supply that generates a DC current to drive one or more electro-thermal TEK cooling device(s). For a cooling device that is capable of generating a 30° C. delta between the two sides of the device, for example, the electrodes could be maintained at 5° C. with an ambient temperature of 35° C. This may be accomplished by maintaining one side of the TEK at ambient temperature using, for example, the Fan unit shown in FIG. 9a, which supplies ambient air flow to the electrodes. The input power to the Fan unit is supplied by the AC power supply unit. The AC power supply unit may supply, for example, a voltage that is proportional to the temperature of the electrodes. This allows noise and power to be optimized such that a desired temperature is achieved at the target tissue. It will be appreciated that alternative methods of cooling (including various heat sinks liquid cooling methods, and the like) may be used in the devices disclosed herein.

The AC power supply unit may supply all the needed voltages and currents for the various components of the device. The input voltage range for the AC power supply unit is preferably within the standard range, i.e., AC 95V-230V. The output voltages and currents will vary according to the needs of the components, and may include: +3.3V at 5 A, +12V at 2 A, and +0V to 60V at 8 A, with such voltages and currents being supplied to each component and/or each of multiple RF generators.

The control interface unit allows control of the device by the user, such as a medical practitioner (for devices intended for hospital use) or an individual (for devices intended for personal use such as hair removal devices) and may include a computer interface, digital controls and displays, analog dials and controls, and the like. Such controls include, for example, power ON/OFF, control of menu setting, emergency power OFF push button, Power inlet, etc.

In FIG. 9b, another PCRF device is shown. This device is similar to the device shown in FIG. 9a, except that a single RF generator is used, the output of which is supplied to multiple phase shift modules to generate different electrical phases at the electrodes. In instances where a relatively large number of different phases are desired or required, the approach exemplified by the device in FIG. 9b may be relatively more economical as compared with the approach exemplified by the device in FIG. 9a.

In FIG. 9c, another PCRF device (particularly suitable for cases in which low power is needed) is shown. A semiconductor chip with a custom package of VFBGA (very fine pitch ball grid array) type circuitry can be used to control the electrodes, RF generator, RF phase control unit, microcontroller unit, fan control unit and control interface unit. The system comprises a power supply unit, the custom semiconductor chip and relatively few buttons on a control unit for human interface. In the example shown, the control unit and power unit electrically attach to the semiconductor chip via a minimal number of wires, as appropriate.

Example 2

Example Configurations of Electrosurgical Device

Figure 13:
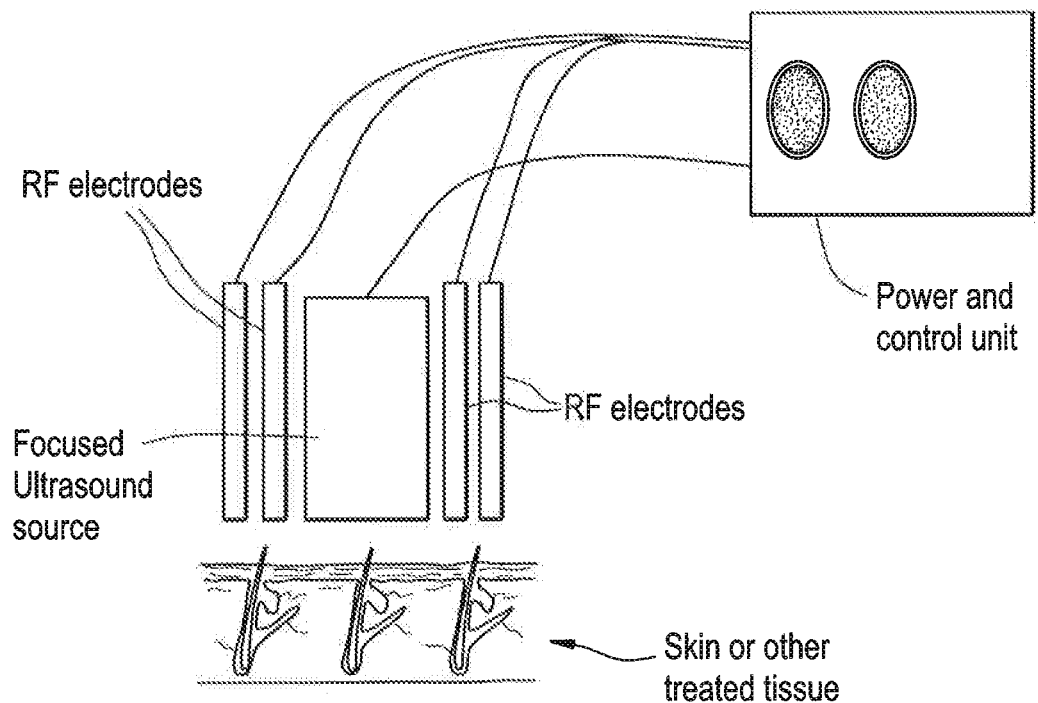
FIG. 13 is an example illustration of an electrosurgical device incorporating ultrasonic energy.

An example configuration of a phase controlled RF device is shown in FIG. 13. A focused ultrasound emitter is coupled with 2 pairs of electrodes (2 on each side, in the example shown) that are supplied with phase controlled RF energy. During treatment of living tissue (e.g., hair removal) both phased RF and ultrasound energies are emitted simultaneously. The applied energy and physical properties of the target tissue cause overheating of the hair shaft and a bulge to form in comparison to surrounding skin. This allows a selective pigment and/or hair removal system.

Example 3

Treatment of Hair Model using Phased RF Energy

Nylon fishing thread was used as a simulator (i.e., model) for hair. The nylon thread is similar to hair in that it has similar diameter, does not absorb water, and is non-conductive. Other simulators that were tried are cotton thread and a metallic needle.

The tissue model used was chicken breast. When implanted in the model, nylon thread maintains the electrical property of being non-conductive. An infrared camera allowing a resolution of 100 μm was used to take real-time images of the model.

An electrosurgical probe comprising 4 electrodes was used in phase-controlled mode. The results were compared with results obtained from the same electrosurgical probe operating in a regular 2-electrode bipolar mode (i.e., only 2 electrodes were powered and the RF energy was not phase-controlled). In the regular bipolar 2-electrode setting, the electrosurgical device did not show selective heating of the hair model. The nylon thread remained cooler than the surrounding tissue. In the phase-controlled mode, the electrosurgical device showed selective heating of the hair model. The temperature of the nylon thread was found to be 20-40° C. warmer than the surrounding tissue.

What is claimed is:

1. A system for heating tissue below the surface of the skin, the system comprising:
a probe including a surface configured to contact the surface of the skin;
at least three electrodes provided along the surface;
a power source configured to supply power to the electrodes and deliver RF currents to the tissue below the surface of the skin via at least three of the electrodes; and
a phase control unit arranged to control a phase between the RF currents to create regions of elevated temperature below the surface of the skin, the elevated temperature being with respect to the surface of the skin.

2. The system of claim 1, arranged to deliver a first RF current below a second RF current.

3. The system of claim 1, wherein the phase control unit is arranged to control the elevated temperature by controlling the phase between the RF currents.

4. The system of claim 1, arranged to heat a skin volume extending between 0.1-50 μm below the skin surface to between 1-4000 μm below the skin, respectively.

5. The system of claim 1, further arranged to deliver at least a part of the RF currents perpendicularly to the skin surface.

6. The system of claim 1, arranged to heat a narrow skin volume with respect to a size of the probe holding the electrodes.

7. The system of claim 1, arranged to heat a skin volume comprising at least a dermis region.

8. The system of claim 1, arranged to heat a skin volume comprising at least a hair follicle or a hair.

9. The system of claim 1, arranged to heat a plurality of focal regions in the heated tissue.

10. The system of claim 1, wherein the phase control unit comprises a feedback loop with respect to at least one measured parameter.

11. The system of claim 10, wherein the at least one measured parameter comprises at least one of: electrical impedance and/or admittance of the skin tissue, the currents flowing between electrodes, electrical potentials between the electrodes, output voltages and phases of the at least one generator, and phase differentials between the generators, when the power source comprises two or more generators.

12. The system of claim 10, wherein the phase control unit comprises a phase locked loop (PLL) element.

13. The system of claim 1, wherein the at least three electrodes are linearly arranged.

14. The system of claim 13, wherein the at least three electrodes comprise at least a first pair of electrodes between electrodes of a second pair of electrodes.

15. The system of claim 13, wherein the at least three electrodes comprise at least two pairs of electrodes having a common electrode.

16. The system of claim 1, further comprising a vibration unit arranged to controllably vibrate at least a part of the probe holding the electrodes.

17. The system of claim 1, further comprising a cooling unit arranged to cool the skin surface.

18. The system of claim 1, further comprising an additional energy source arranged to apply to the skin at least one of: coherent or incoherent visible light, infrared radiation, ultraviolet radiation, and ultrasound.

19. A method of heating tissue below the surface of the skin, comprising:
delivering RF currents to a skin target via at least three electrodes associated with a probe and receiving power from a power source, and
controlling a phase between the RF currents to create regions of elevated temperature below the surface of the skin, the elevated temperature being with respect to the surface of the skin.

20. The method of claim 19, further comprising delivering a first RF current below a second RF current.

21. An electrosurgical system comprising:
an electrosurgical probe for applying at least a heat treatment to tissue of a patient below the surface of the skin, the probe being configured to contact the surface of the skin and comprising at least one substantially straight row of electrodes, the at least one row of electrodes including at least a first electrode, a second electrode, and a third electrode; and
a generator comprising a plurality of RF outputs and phase controlling circuitry for controlling the phase therebetween, wherein connection between the RF outputs and the electrodes is configured such that at least two electrode pairings are formed, the at least two electrode pairings including a first pair comprising the first and second electrodes, and the second pair comprising the first and third electrodes,
wherein the phase controlling circuitry is configured such that the RF outputs apply a respective RF electrical potential across each pairing at a phase, and
wherein the phase between pairings results in electrical currents being established between at least one of the pairings at an angle to the surface of the skin causing heating of the tissue below the surface of the skin.

22. The System according to claim 21, wherein the angle is substantially perpendicular.

23. The electrosurgical system of claim 21, wherein the electrodes in cross section are substantially rectangular, and wherein the electrodes are disposed on the treatment surface such that there is at least between about 0.01 mm and about 25 mm between the centers of any two electrodes.

24. The electrosurgical system of claim 21, wherein the RF energy causes elevation of the temperature within columns of the tissue, the columns of tissue being substantially perpendicular to a surface of the tissue.

25. The electrosurgical system of claim 21, further comprising a means for adjusting the electrical currents in the living tissue in response to a measured characteristic of the current in the living tissue.

26. The electrosurgical system of claim 25, wherein the measured characteristic is selected from the magnitude, time-integration, first derivative with respect to time, and second derivative with respect to time.

27. An electrosurgical system comprising:
an electrosurgical probe for applying at least a heat treatment to tissue of a patient below the surface of the skin, the probe being configured to contact the surface of the skin and comprise at least one substantially straight row of electrodes, the at least one row of electrodes including a first pair of electrodes and a second pair of electrodes, wherein the second pair of electrodes is arranged along the row to sandwich the first pair of electrodes; and
a generator comprising at least first and second RF outputs and phase controlling circuitry;
wherein each RF output provides power to a respective pair of the first and second pair of electrodes, the phase controlling circuitry being configured for effecting a phase between the first and second RF outputs such that electrical currents are established between at least the second pair of electrodes which are at an angle to the surface of the skin, and wherein the electrical currents result in heating of the tissue below the surface of the skin for treatment thereof.

28. The System according to claim 27, wherein the angle is substantially perpendicular.

29. The electrosurgical system of claim 27, wherein the electrodes in cross section are substantially rectangular, and wherein the electrodes are disposed on the treatment surface such that there is at least between about 0.01 mm and about 25 mm between the centers of any two electrodes.

30. The electrosurgical system of claim 27, wherein the RF energy causes elevation of the temperature within columns of the tissue, the columns of tissue being substantially perpendicular to a surface of the tissue.

31. The electrosurgical system of claim 27, further comprising a means for adjusting the electrical currents in the living tissue in response to a measured characteristic of the current in the living tissue.

32. The electrosurgical system of claim 31, wherein the measured characteristic is selected from the magnitude, time-integration, first derivative with respect to time, and second derivative with respect to time.

* * * * *